United States Patent
Frame et al.

(10) Patent No.: US 6,689,927 B1
(45) Date of Patent: Feb. 10, 2004

(54) PROCESS FOR OLIGOMER PRODUCTION AND SATURATION

(75) Inventors: Robert R. Frame, Glenview, IL (US); Laurence O. Stine, Western Springs, IL (US); Hayim Abrevaya, Wilmette, IL (US)

(73) Assignee: UOP LCC, Des Plaines, IL (US)

( * ) Notice: Subject to any disclaimer, the term of this patent is extended or adjusted under 35 U.S.C. 154(b) by 128 days.

(21) Appl. No.: 09/850,471

(22) Filed: May 7, 2001

(51) Int. Cl.[7] .............................. C07C 2/06; C07C 2/08; C07C 2/14; C07C 2/18

(52) U.S. Cl. ...................... 585/510; 585/514; 585/520; 585/529

(58) Field of Search ................................ 585/510, 514, 585/520, 524

(56) References Cited

U.S. PATENT DOCUMENTS

| | | | |
|---|---|---|---|
| 2,526,966 A | 10/1950 | Oberfell et al. ................. 196/1 |
| 3,832,418 A | 8/1974 | Bercik et al. ....... 260/683.15 R |
| 4,197,185 A | 4/1980 | Le Page et al. ............... 208/71 |
| 4,225,743 A | 9/1980 | Hoshiyama et al. ........ 585/512 |
| 4,244,806 A | 1/1981 | Le Page et al. ............... 208/49 |
| 4,304,948 A | 12/1981 | Vora et al. ................... 585/315 |
| 4,324,646 A | 4/1982 | Le Page et al. ............... 208/71 |
| 4,393,259 A | 7/1983 | Ward et al. .................. 585/315 |
| 4,463,211 A | 7/1984 | Manning ..................... 585/510 |
| 4,469,911 A | 9/1984 | Manning ..................... 585/515 |
| 4,749,820 A | 6/1988 | Kuo et al. ................... 585/330 |
| 5,049,360 A | 9/1991 | Harandi et al. ............. 422/141 |
| 5,176,719 A | * 1/1993 | Harandi et al. ................ 44/449 |
| 5,338,889 A | * 8/1994 | Vora et al. ................... 568/697 |
| 5,414,160 A | * 5/1995 | Sato et al. ................... 524/296 |
| 5,877,372 A | 3/1999 | Evans et al. ................. 585/510 |
| 5,895,830 A | 4/1999 | Stine et al. .................. 585/259 |
| 5,990,367 A | 11/1999 | Stine et al. .................. 585/514 |
| 5,994,601 A | 11/1999 | Nierlich et al. ............. 585/329 |
| 6,080,903 A | 6/2000 | Stine et al. .................. 585/514 |

* cited by examiner

Primary Examiner—Thuan D. Dang
(74) Attorney, Agent, or Firm—John G. Tolomei; James C. Paschall

(57) ABSTRACT

A process for the production of $C_8$ alkenes with high selectivities to 2,4,4-trimethylpentene by the oligomerization of isobutene and/or n-butene at lower temperatures is disclosed. Higher proportions of heavy paraffins mixed with the butene feed in the oligomerization zone improve the selectivity to 2,4,4-trimethylpentene along with better selectivity to octene and lower selectivity to dodecene. Additionally, we have found that n-butene codimerizes with isobutene selectively to 2,4,4-trimethylpentene.

18 Claims, 1 Drawing Sheet

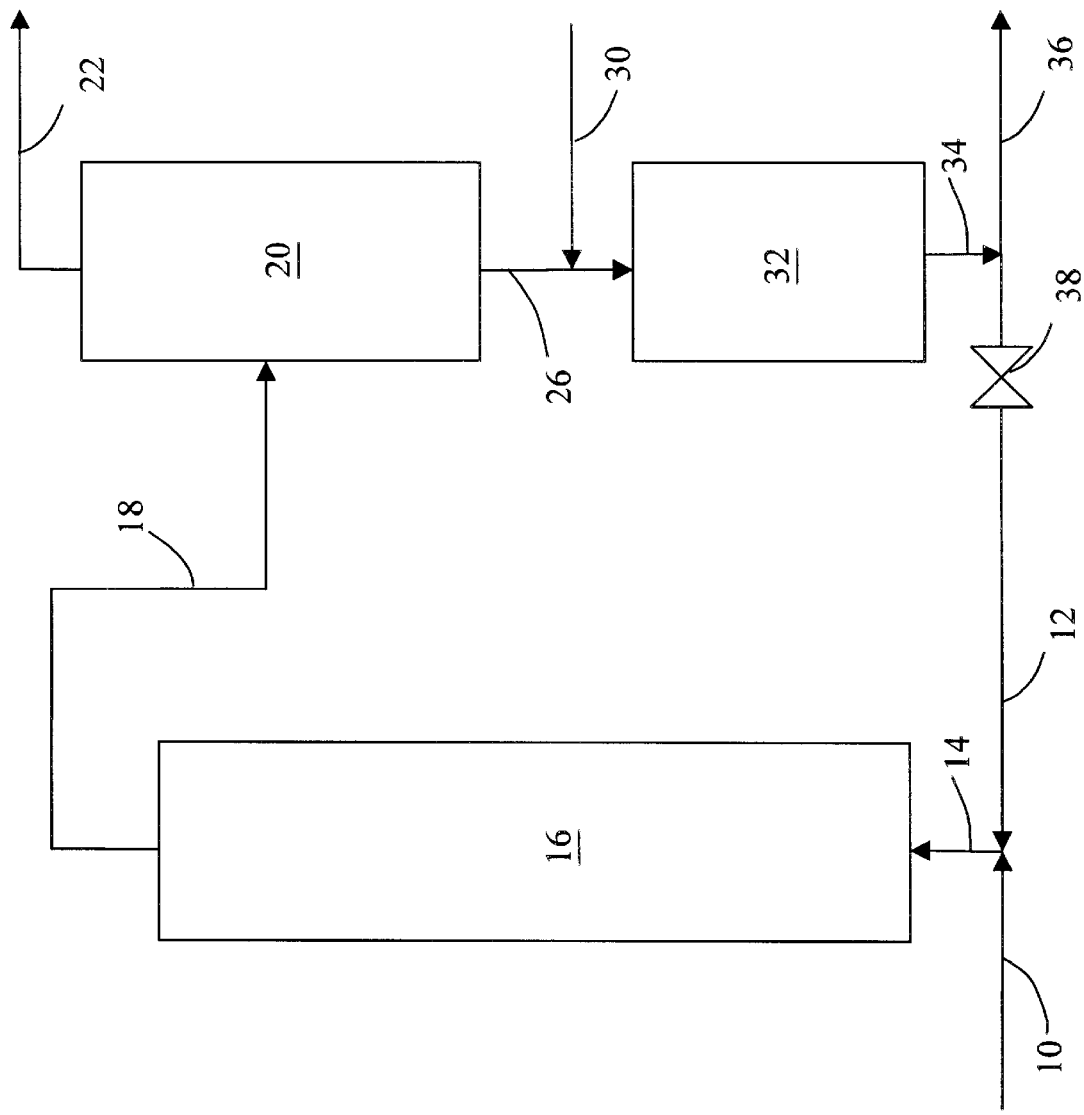

PROCESS FOR OLIGOMER PRODUCTION AND SATURATION

FIELD OF THE INVENTION

This invention relates generally to the production of octene isomers by the oligomerization of butene. Specifically, the invention relates to the oligomerization of butene to high selectivities of octene isomers and, specifically, to 2,4,4-trimethylpentene.

BACKGROUND OF THE INVENTION

Processes for the oligomerization of lighter olefins to produce $C_8$ oligomers are known. Oligomerization processes have been long employed to produce good quality motor fuel from butene. Such oligomerization processes are also referred to as catalytic condensation and polymerization with the resulting motor fuel often referred to as polymer gasoline. Methods have always been sought to improve the octane number of the gasoline boiling range oligomerization products. In addition, the oligomerization process is also susceptible to catalyst fouling from the condensation of heavy oligomers into coke that covers the catalyst.

Another process that has met the continuing demand for the conversion of light hydrocarbons into high octane motor fuels was the alkylation of isobutane with propylene, butenes and amylenes using a hydrofluoric acid (HF) catalyst, commonly referred to as HF alkylation. The HF process has provided a highly successful method for the production of high octane motor fuels.

A number of arrangements are known for using oligomerization in combination with other processes such as saturation and dehydrogenation as substitutes for acid catalyzed isomerization alkylation. Patents disclosing the dehydrogenation of light paraffin stream with oligomerization of the dehydrogenation effluent include U.S. Pat. No. 4,393,259 B1, U.S. Pat. No. 5,049,360 B1, U.S. Pat. No. 4,749,820 B1, U.S. Pat. No. 4,304,948 B1 and U.S. Pat. No. 2,526,966 B1.

Trimethylpentenes are the preferred product in the production of gasoline. High selectivities to trimethylpentenes, and specifically to 2,4,4-trimethyl-1-pentene and 2,4,4-trimethyl-2-pentene, are desired because they can be hydrogenated to 2,2,4-trimethylpentane which has a very high research and motor octane numbers.

TABLE 1

| $C_8$ Isomer | Research Octane Number | Motor Octane Number |
| --- | --- | --- |
| 2,2,4-trimethylpentane | 100 | 100 |
| 2,3,4-trimethylpentane | 102.7 | 95.9 |
| 2,2,3-trimethylpentane | 109.6 | 99.9 |
| 2,3,3-trimethylpentane | 106.1 | 99.4 |

Isomers of 2,4,4-trimethylpentene typically include 2,4,4-trimethyl-1-pentene and 2,4,4-trimethyl-2-pentene but will hereinafter be collectively referred to as 2,4,4-2-trimethylpentene. Among the trimethylpentanes, 2,2,4-trimethylpentane is desired when a high vapor pressure gasoline blending stock is desired because it has a relatively low boiling point and a relatively high vapor pressure.

TABLE 2

| $C_8$ Isomer | Boiling Point at 1 atm (° C.) |
| --- | --- |
| 2,2,4-trimethylpentane | 99.2 |
| 2,3,4-trimethylpentane | 113.5 |
| 2,2,3-trimethylpentane | 109.8 |
| 2,3,3-trimethylpentane | 114.8 |

U.S. Pat. No. 5,877,372 B1 endeavors to oligomerize to diisobutene by dimerization of pure isobutene. Diisobutene is typically 2,4,4-trimethylpentene, but it tends to isomerize to 2,3,4-trimethylpentene. Affordable feedstocks for butene oligomerization processes are typically provided by one of the effluent streams from a fluidized catalytic cracking unit which usually includes a mixture of isobutene, n-butene and butane. Hence, dimerization of pure isobutene is not typically feasible.

Efforts in the prior art to increase the selectivity to 2,4,4-trimethylpentene from butene mixtures typically involve attempting to encourage the dimerization of isobutene and suppress both the dimerization of n-butene and the co-dimerization of isobutene and n-butene. U.S. Pat. No. 4,469,911 B1 discloses oligomerizing isobutene and n-butene together over a resin catalyst at lower temperatures. The lower temperatures are reported to favor selective dimerization of isobutene with itself to produce isobutene dimer or diisobutene rather than the codimerization of isobutene with n-butene to produce codimers or subsequent oligomerization to produce trimers. Although this process is reported to produce a selectivity to 2,4,4-trimethylpentene as high as 86.2 liquid volume percent, the attendant selectivity to dodecene was as high as 12.2 liquid volume percent. Dodecene in the product lowers octane numbers and lowers vapor pressure.

Other patents disclose oligomerizing a mixture of n-butenes and isobutenes under conditions that encourage isobutene dimerization and discourage n-butene dimerization. In U.S. Pat. No. 4,197,185 B1, U.S. Pat. No. 4,244,806 B1 and U.S. Pat. No. 4,324,646 B1, a cut including isobutene, n-butene and butane is oligomerized over an alumina based catalyst such that the isobutene has at least a 90% conversion and the n-butene has lower than a 16% conversion. This method capitalizes on the slower rate of n-butene reactions. U.S. Pat. No. 3,832,418 B1 also discloses a selective dimerization process in which a mixture of n-butenes and isobutenes oligomerize over a catalyst comprising presulfided nickel fluorine on a silica-alumina support with over 80% conversion of isobutene and less than 5% conversion of n-butene. U.S. Pat. No. 5,994,601 B1 discloses oligomerizing a mixture of n-butenes and isobutenes while endeavoring to separate dimers of the n-butenes from dimers of isobutene.

Contrarily, other patents focus on n-butene dimerization. U.S. Pat. No. 4,225,743 B1 discloses codimerizing isobutene with n-butene to form methylheptenes and dimethylhexenes and suppress the formation of 2,4,4-trimethylpentene by using a specific nickel catalyst solution and an organo-aluminum catalyst. U.S. Pat. No. 4,463,211 B1 discloses that dimerization of n-butenes in the presence of minimal isobutenes over a cation exchange resin yields primarily dimethylhexenes. Pimethylhexene reduces the octane number of gasoline.

The indirect alkylation process described in U.S. Pat. No. 6,080,903 B1, U.S. Pat. No. 5,990,367 B1 and U.S. Pat. No. 5,895,830 B1 dimerizes mixtures of n-butene and isobutene over a solid phosphoric acid (SPA) catalyst in the presence of a higher paraffin diluent such as cyclohexane or octane. The presence of the paraffin diluent is believed to promote the oligomerization in the liquid phase to yield predominantly dimerized butene oligomers such as $C_8$ olefins. The liquid phase washes deactivating components from the catalyst to prolong catalyst life. The higher aliphatic olefins can be saturated to provide high octane fuel. The process gives high butene conversion with octene selectivities as high as 87.2 wt-% and selectivities to trimer products as low as 11.7 wt-%. These patents recommend that operating temperatures in a narrow range of 300° to 400° F. (149° to 204° C.) increase the selectivity of $C_8$ olefins.

Even in the context of indirect alkylation, mechanistic theory predicts that in a reaction mixture of isobutene and n-butene in the presence of a SPA catalyst, the isobutene will dimerize with itself to produce 2,4,4-trimethylpentene and isobutene will co-dimerize with n-butene to produce 2,2,3-trimethylpentene. Moreover, the desired 2,4,4-trimethylpentene also has a tendency to shift to 2,3,4-trimethylpentene.

Hence, it is an object of the present invention to run an oligomerization of butene in the presence of a catalyst so as to obtain a desired selectivity to 2,4,4-trimethylpentene from an oligomerization of butenes. It is a further object of this invention to oligomerize a mixture of n-butene and isobutene to obtain a high selectivity to 2,4,4-trimethylpentene. It is a still further object of the present invention to minimize the production of dodecene.

BRIEF SUMMARY OF THE INVENTION

It has been surprisingly found that very high yields of octenes and, specifically, 2,4,4-trimethylpentene, with attendant low selectivity to dodecene are produced from the dimerization of isobutene and/or mixtures of isobutene and n-butene when diluted with a paraffinic diluent. We have surprisingly found that higher conversion of n-butene with isobutene does not diminish the selectivity to 2,4,4-trimethylpentene. In light of earlier belief, we were surprised to find that high selectivity to octene can be achieved at lower temperatures, such as below 250° F. (121° C.). Moreover, we found that by diluting the oligomerization conditions with more paraffinic diluent, octene selectivity exceeds 98% and 2,4,4-trimethylpentene selectivity exceeds 77 wt-%, while producing less than 0.9 wt-% dodecene.

In one embodiment, the present invention relates to a process for oligomerizing isobutene and n-butene to a product comprising a high selectivity to 2,4,4-trimethylpentene. The process comprises passing an olefinic feed comprising isobutene and n-butene to an oligomerization zone and contacting the olefinic feed with an oligomerization catalyst at oligomerization conditions including a reaction temperature of 250° F. (121° C.) or less. A saturate stream comprising paraffins having a carbon number of at least 6 is passed into the oligomerization zone with the olefinic feed and the catalyst at a predetermined weight ratio of the saturate stream to the olefinic feed. An effluent stream including product exhibiting a greater selectivity to 2,4,4-trimethylpentene than an effluent stream from a process with substantially the same conditions but with a smaller weight ratio of saturate stream to olefinic feed is recovered from the process.

In another embodiment, the present invention relates to an oligomerization process with a high selectivity to 2,4,4-trimethylpentene. The process comprises passing an olefinic feed comprising n-butene and isobutene to an oligomerization zone and contacting the olefinic feed with a solid phosphoric acid catalyst at oligomerization conditions including a reaction inlet temperature of no greater than 250° F. (121° C.). A saturate stream comprising paraffins having a carbon number of at least 6 is passed into the oligomerization zone with the olefinic feed and the catalyst. An effluent stream including product exhibiting a selectivity to 2,4,4-trimethylpentene of at least 40 wt-% is recovered from the process.

In a further embodiment, the present invention relates to an oligomerization process with a high selectivity to octene and a low selectivity to dodecene in an effluent stream. The process comprises passing an olefinic feed comprising butene to an oligomerization zone and contacting the olefinic feed with an oligomerization catalyst at oligomerization conditions including a reaction temperature of 250° F. (121° C.) or less. A saturate stream comprising paraffins having a carbon number of at least 6 is passed into the oligomerization zone with the olefinic feed and the catalyst. An effluent stream comprising the paraffins and a product exhibiting a selectivity to octene of at least 80 wt-% and a selectivity to dodecene of 11 wt-% or less is recovered from the process.

Other objects, embodiments and details of this invention will be provided in the following detailed disclosure of the invention.

BRIEF DESCRIPTION OF THE DRAWING

The FIGURE is process flow diagram showing a basic schematic arrangement in which this invention may be used.

DETAILED DESCRIPTION OF THE INVENTION

The essential operational zone for the practice of this invention is the oligomerization reaction zone. Suitable oligomerization zones for this invention take on many forms. The oligomerization process is known by many names such as catalytic condensation and also catalytic polymerization. Known catalysts for effecting such reactions include heterogeneous catalyst such as solid acids and homogenous catalysts, in particular halogenated catalysts such as boron trifluoride as described in U.S. Pat. No. 3,906,053 B1, U.S. Pat. No. 3,916,019 B1 and U.S. Pat. No. 3,981,941 B1.

Preferred catalyst for the oligomerization can generally be described as protonic acids. The preferred acids will generally have a Hammett acidity function of less than −4.0 and preferably of about −5.0 or less. A particularly preferred catalyst is a solid phosphoric acid (SPA) catalysts which has a Hammett acidity function of approximately −5.0 or lower. The SPA catalyst refers to a solid catalyst that contains as a principal ingredient an acid of phosphorous such as ortho-, pyro- or tetraphosphoric acid.

SPA catalyst is normally formed by mixing the acid of phosphorous with a siliceous solid carrier to form a wet paste. This paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives such as mineral talc, fuller's earth, and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this composition such as a lower phosphoric acid content are however possible. Further details as to the composition and production of SPA catalysts may be obtained from U.S. Pat. No. 3,050,472 B1, U.S. Pat. No. 3,050,473 B1, U.S. Pat. No. 3,132,109 B1 and from other references.

Oligomerization zones in general are maintained at conditions which may vary widely due to the previously listed variables. We have found that improved selectivities to octene and, specifically 2,4,4-trimethylpentene, result at the lower end of the range of reaction temperatures previously published for use in the indirect alkylation processes. The 2,4,4-trimethylpentene isomers comprise 2,4,4-trimethyl-1-pentene and 2,4,4-trimethyl-2-pentene but are collectively referred to as 2,4,4-trimethylpentene, herein. A suitable temperature of the oligomerization reaction zone will typically be in a range of from 140° to 250° F. (60° to 121° C.) and will more typically be in a range of from 160° to 195° F. (71° to 91° C.). When practicing this invention, a reaction temperature of about 167° to 185° F. (75° to 85° C.) is preferred. Pressures within the oligomerization reaction zone will usually be in a range of from 100 to 1200 psig (690 to 8274 kPa) and more typically in a range of from 200 to 1000 psig (1379 to 6895 kPa). When practicing this invention the preferred operating pressure for the SPA catalyst will be in a range of from 400 to 600 psig (2758 to 4137 kPa) with 450 to 550 psig (3103 to 3792 kPa) being particularly preferred.

The feed to the oligomerization zone reaction will typically comprise $C_4$ olefins and aliphatics with some $C_3$ and $C_5$ olefins and aliphatics. Steam or water may be fed into the reactor to maintain a low water content for hydration of the preferred SPA catalyst. The source of the $C_4$ feed may be a light gas stream recovered from the gas separation section of a fluidized catalytic cracking (FCC) process, $C_4$ streams from steam cracking and coker off gas or the effluent from a dehydrogenation zone. In most operations, the feed stream will comprise n-butenes, isobutenes and n-butanes and/or isobutanes. The principal reaction will involve isobutene. However, in the present invention, greater conversion of n-butenes at equivalent total butene conversion results in greater yields and selectivities to octene and 2,4,4-trimethylpentene with smaller yields and selectivities to dodecene. Preferably, out of the total olefin concentration in the feed stream, at least 30 wt-% and more preferably at least 60 wt-% will comprise isobutene. Similarly, the total olefin concentration in the feed stream will preferably include at least 20 wt-% and more preferably at least 40 wt-% n-butene. N-butane or isobutane will make up the remainder of the $C_4$ hydrocarbons in the feed.

In the practice of this invention, heavy paraffin diluent contacts the catalyst in conjunction with the usual oligomerization zone feed. The heavy paraffin diluent will comprise hydrocarbons having at least six carbon atoms, and preferably at least 8 carbon atoms, and up to twenty carbon atoms and will preferably comprise $C_6$ to $C_8$ paraffins. Addition of a heavy paraffin stream will provide a substantial quantity of heavy paraffins in the oligomerization zone. $C_8$ paraffins are particularly preferred because product octenes can be hydrogenated, and the resulting octanes be recycled from a downstream hydrogenation zone back to the reactor as paraffinic diluent. Hence, $C_8$ will preferably comprise 10 to 90 wt-% of the mass flow through the oligomerization reaction zone.

A way of quantifying the amount of paraffinic diluent added to the oligomerization zone is through a parameter termed a combined feed ratio (CFR). The CFR is the ratio of the sum of the fresh feed rate and the paraffinic diluent feed rate to the oligomerization zone to the fresh feed rate to the oligomerization zone.

$$CFR = \frac{\text{Fresh Feed Rate} + \text{Paraffinic Diluent Feed Rate}}{\text{Fresh Feed Rate}}$$

We have found that the greater the CFR at lower reaction temperatures, the greater the yield and selectivity to 2,4,4-trimethylpentene as well as to octene and the lower the yield and selectivity to dodecene. Hence, it is preferred to operate at a CFR of at least 5 and preferably 8 or greater. When higher concentrations of butane or other light paraffins are present in the feed, the same selectivity improvements may possibly be obtained without utilizing a CFR that is as high as required with lower concentrations of light paraffins. Hence, the benefits that raising the CFR provides may be partially attributed to high concentrations of light paraffins. However, we have found that a given quantity of heavy paraffins of $C_6$ and greater does much more for selectivity to desired products than the same quantity of light paraffins. Nonetheless, for a given quantity of light paraffins in the feed, the greater the CFR, the higher the selectivity to 2,4,4-trimethylpentene.

A higher CFR also results in more of the n-butene conversion and less of the isobutene conversion at an equivalent overall butene conversion. Mechanistic theory would predict that codimerization of n-butene and isobutene would yield 2,2,3-trimethylpentene. However, greater conversion of n-butene results in greater yield of 2,4,4-trimethylpentene and lower yield of 2,2,3-trimethylpentene. Hence, we believe that at higher CFRs and/or at the lower temperature of the present invention, conventional mechanistic theory is inaccurate. While not wishing to be bound by any particular theory, we believe that in the present invention codimerization of n-butene and isobutene yield 2,2,3-trimethylpentene which undergoes a 1,2 methyl shift to finally yield 2,4,4-trimethylpentene.

We have also found that selectivity to 2,3,4-trimethylpentene is lower under the conditions of the present invention. Normally, 2,4,4-trimethylpentene has a tendency to shift to 2,3,4-trimethylpentene. However, when CFR is increased, the selectivity to 2,3,4-trimethylpentene decreases while selectivity to 2,4,4-trimethylpentene increases.

The presence of the heavy paraffins are believed to promote liquid phase conditions in the oligomerization zone. The combined heavy paraffinic stream and feed will usually maintain at least partial liquid phase conditions in the oligomerization zone. Partial liquid phase conditions refers to maintaining at least 10 wt-% of the combined paraffinic stream and fresh feed in liquid phase. Preferably, at least 50 wt-% of the combined fresh feed and paraffinic stream are in liquid phase in the oligomerization zone to provide substantial liquid phase conditions, and more preferably essentially all, i.e. at least 90 wt-%, of the fluid in the oligomerization zone will be in liquid phase.

The heavy paraffin diluent may enter the process with the incoming feed or may be injected into an oligomerization reaction zone at intermediate locations within a single catalyst bed or a number of catalyst beds. It is preferred to have the heavy paraffins present as the feed initially enters the reaction zone to maximize the benefit of the heavy paraffins in the process. Additional quantities of the heavy paraffins may be injected in stages through process to maintain temperature control throughout the bed or beds of oligomerization catalyst.

The present invention may be performed in any suitable reactor. Where the oligomerization zone has a multiple bed arrangement, the different catalyst beds are preferably contained within one or more cylindrical, vertically oriented vessels. The catalyst is preferably disposed in fixed beds within the oligomerization zone in what is known as a chamber-type reactor structure. Typically, a chamber-type reactor will contain about five, large diameter catalyst beds, through which the reactants will flow. The temperature of the reactants are controlled by the paraffinic diluent which acts as a heat sink. Oligomerization reaction zones may be arranged with such multiple beds of catalyst that receive an intermediate injection of the paraffinic diluent to serve also as a quench material to control temperatures from the exothermic reaction. In a chamber reactor, the feed stream preferably enters the bottom of the reactor and operates in the upflow mode to ensure plug flow. However, if the invention is performed in a tube reactor, upflow may not be necessary to ensure plug flow.

The effluent from the oligomerization reaction zone will normally enter a separator. In the separator, the lighter components will be separated from the heavier components. In an embodiment, the heavy components will be saturated. A portion of the saturated heavy components will be recycled as a paraffinic diluent to the oligomerization zone. The remaining portion will be blended with a gasoline feedstock. Unless otherwise noted, the term "portion" when used herein to describe a process stream refers to either an aliquot portion of the stream or a dissimilar fraction of the stream having a different composition than the total stream from which it was derived.

When present in the process, preferred saturation reaction zones will provide an essentially complete saturation of all olefins from the saturation reactor. The circulation of the heavy paraffin recycle can offer the added advantage of permitting the oligomerization zone to operate at lower pressure. In some cases it may be possible to use the lower pressure operation of the oligomerization reactor for direct passage of the polymerization effluent to the hydrogenation reactor. Exothermicity will typically cause the saturation zone to operate at higher temperatures than the oligomerization zone so that quench fluid and paraffins in the effluent from the oligomerization will provide additional heat sink material for the heat release of the saturation reaction zone.

A process flow scheme in which the present invention may be used will be described in conjunction with the FIGURE. However, other process flow schemes incorporating the present invention other than shown and described may be used. The FIGURE shows only a limited form of a process flow scheme incorporating the present invention and only those portions of the process that are necessary to gain an understanding of the invention and the necessary means of integrating the principal processing steps that comprise the invention. Further details related to valves, control means, pumps, compressors, coolers and other necessary processing equipment are well known to those skilled in the art and not described in detail unless necessary for an understanding of the invention.

An oligomerization zone feed stream, rich in $C_4$ olefins and in particular at least isobutene and probably n-butene, isobutane and/or n-butane, is brought into the process by a line 10 and combined with a recycle stream of $C_8$ paraffins carried by a line 12. Line 10 may carry oligomerization feed from a dehydrogenation zone (not shown) but other previously mentioned sources of feed, such as a $C_4$ cut from an FCC fractionation unit, are also suitable. Line 14 carries the combined feed and recycle paraffin stream into an oligomerization reactor 16 wherein the feed and paraffins contact a catalyst, which is preferably SPA. The oligomerization reactor 16 comprises a chamber reactor through which upflow is preferred to ensure plug flow. Oligomerization reactor 16 can comprise tubing, pipes, jets or other common means for introducing reactants into the reaction zone of the reactor.

A stream 18 carries an oligomerization effluent of lighter components, primarily comprising unreacted butanes and butenes, and heavy components comprising higher olefins, of mainly octene, some dodecene and heavy paraffins comprising primarily octanes and some dodecanes out the oligomerization reactor 16 to a separator 20. Separator 20 separates lighter components from the heavy components. Separator 20 may provide a simple flashing operation to make a rough cut of the heavy stream or may be a fractionation zone. A line 22 carries the lighter components olefins from separator 20 for further processing. Further processing could include recycling a portion of line 22 comprising both butenes and butanes back to the line 10 as fresh feed, separating butenes from butanes and recycling the butenes back to line 10 as fresh feed, or forwarding line 22 to a direct alkylation unit. A bottoms stream containing the heavy components of higher olefins and heavy paraffins is withdrawn from the separator 20 by a line 26. The heavy paraffins and higher olefins are combined with hydrogen from a line 30 and passed to a saturation reactor 32.

Line 30 supplies hydrogen to the saturation zone and should contain at least 50 wt-% of hydrogen. Preferably, the hydrogen-containing gas stream will have a hydrogen concentration greater than 75 wt-% hydrogen. Hydrogen can be conveniently recovered from a dehydrogenation zone which may supply a portion of the olefins for the oligomerization zone or outside sources may supply all of the necessary hydrogen when a saturation zone is present. Preferably the saturation zone will operate with a minimum excess of hydrogen.

The saturation reactor 32 saturates the higher olefins, comprising primarily octenes, to heavy paraffins, comprising primarily octane. The heavy paraffins in the line 26 are not significantly affected in saturation reactor 32. Saturation zone effluent will exit thorough line 34, and will have a greater proportion of heavy paraffins than the stream entering the saturation reactor 32 than through line 26. A portion of the octanes are withdrawn through line 36 to be blended with gasoline feed stock. Line 12 recycles the other portion of saturated olefins back to the oligomerization reactor 16 to serve as the paraffinic diluent. Valve 38 can be used to control the amount of heavy paraffins recycled back to the oligomerization reactor 16 which affects the CFR and the amount of heavy paraffins withdrawn as end product. By recycling octane, catalyst fouling is reduced in oligomerization reactor 16 and the need for an external source of make-up paraffins is reduced.

To more fully demonstrate the attendant advantages of the present invention, the following tests was performed.

EXAMPLE

We conducted a study that compared oligomerization of two feeds containing the same isobutene to n-butene feed ratio: 0.63. The feeds also contained butane, so that the ratio of butane to butenes was the same in both feeds. Both feeds also contained isooctane diluent to simulate feeds resulting from combining a $C_4$ feed with a recycled paraffinic stream. Isooctane was blended in quantities to simulate CFRs of 2 and 8. The feeds in both cases were composed as follows:

TABLE 3

| CFR | Butene-1 | Butene-2 | Isobutene | N-Butane | Isooctane |
|---|---|---|---|---|---|
| 2 | 2.45 | 3.65 | 3.85 | 2.55 | 12.5 |
| 8 | 2.45 | 3.65 | 3.85 | 2.55 | 87.5 |

These feeds were processed in a downflow tube reactor over solid phosphoric acid catalyst. The processing was performed with a catalyst bed inlet temperature of 176° F. (80° C.) and a plant pressure of 500 psig (3447 kPa). The total feed rate was the same for both feeds and equal to a contact time of 0.4 hours. Actual products were hydrogenated and analyzed to give the results in the following Table 4.

TABLE 4

|  | CFR | |
|---|---|---|
|  | 2 | 8 |
| Butene Conversion (wt-%): | | |
| n-butene | 27 | 37 |
| isobutene | 100 | 82 |
| Total butene | 55 | 54 |
| Octene Selectivity (wt-%) | 96.8 | 98.1 |
| Dodecene Selectivity (wt-%) | 3.1 | 0.9 |
| TMP Selectivities (wt-%): | | |
| 2,2,4-trimethylpentane | 43.6 | 77.5 |
| 2,3,4-trimethylpentane | 19.1 | 4.2 |
| 2,2,3-trimethylpentane | 17.6 | 5.3 |
| 2,3,3-trimethylpentane | 5.7 | 1.0 |

It is clear from the data in Table 4 that superior yields of 2,4,4-trimethyl-pentene (hydrogenated to 2,2,4-trimethylpentane) result at the higher CFR of 8 while holding all other conditions of the process to be substantially the same. Additionally, the other trimethylpentane skeletons decrease in selectivity with the higher CFR. Therefore, the product becomes very rich in 2,4,4-trimethylpentene as the CFR is increased. Additionally, the higher CFR generates better selectivity to octene and lower selectivity to dodecene. Lastly, the higher CFR results in a higher conversion of n-butene and lower conversion of isobutene at the same total butene conversion.

What is claimed is:

1. A process for oligomerizing isobutene and n-butene to a product comprising a high selectivity to 2,4,4-trimethylpentene, said process comprising:

a) passing a feed stream comprising isobutene and n-butene to an oligomerization zone and contacting the feed stream with an oligomerization catalyst at oligomerization conditions;

b) passing a saturate stream, comprising paraffins having a carbon number of at least 6 into said oligomerization zone with said feed stream and said catalyst at a weight ratio of said feed stream and said saturate stream to said feed stream of at least 8; and c) recovering an effluent stream including product exhibiting a greater selectivity to 2,4,4-trimethylpentene than an effluent stream from a process with substantially the same conditions but with a smaller weight ratio of said feed stream and saturate stream to said feed stream.

2. The process of claim 1 wherein a total butene conversion is at least 50 wt-%.

3. The process of claim 1 wherein a selectivity to dodecene is no greater than 11 wt-%.

4. The process of claim 1 wherein a selectivity to octene is over 88 wt-%.

5. The process of claim 1 wherein the n-butene conversion is over 25 wt-%.

6. An oligomerization process with a high selectivity to 2,4,4-trimethylpentene, said process comprising:

a) passing a feed stream comprising n-butene and isobutene to an oligomerization zone and contacting the feed stream with a solid phosphoric acid catalyst at oligomerization conditions including a reaction inlet temperature of no greater than 250° F. (121° C.);

b) passing a saturate stream, comprising paraffins having a carbon number of at least 6 into said oligomerization zone with said feed stream and said catalyst, wherein a weight ratio of said feed stream and said saturate stream to said feed stream is 8 or greater; and c) recovering an effluent stream including product exhibiting a selectivity to 2,4,4-trimethylpentene of at least 40 wt-%.

7. The process of claim 6 wherein the effluent stream is hydrogenated to obtain 2,2,4-trimethylpentane.

8. The process of claim 6 wherein said feed stream includes non-reactive butane.

9. The process of claim 6 wherein a conversion of n-butene is at least 25 wt-%.

10. The process of claim 6 wherein a selectivity to dodecene is no greater than 11 wt-%.

11. The process of claim 6 wherein a selectivity to octene is at least 88 wt-%.

12. An oligomerization process with a high selectivity to octene and a low selectivity to dodecene in an effluent stream, said process comprising:

a) passing a feed stream comprising butene to an oligomerization zone and contacting the feed stream with an acidic oligomerization catalyst at oligomerization conditions including a reaction temperature of 250° F. (121° C.) or less, said oligomerization catalyst having a Hammett acidity function of less than −4;

b) passing a saturate stream, comprising paraffins having a carbon number of at least 6 into said oligomerization zone with said feed stream and said catalyst, wherein a weight ratio of said feed stream and said saturate stream to said feed stream is 8 or greater; and c) recovering said effluent stream comprising said paraffins and a product exhibiting a selectivity to octene of at least 80 wt-% and a selectivity to dodecene of 11 wt-% or less.

13. The process of claim 12 wherein the effluent stream is hydrogenated to obtain octane.

14. The process of claim 13 wherein said oligomerization catalyst is SPA.

15. The process of claim 12 wherein a selectivity to 2,4,4-trimethylpentene is over 70 wt-%.

16. The process of claim 12 wherein a conversion of n-butene is at least 25 wt-%.

17. The process of claim 12 wherein a selectivity to 2,4,4-trimethylpentene is at least 40 wt-%.

18. The process of claim 12 wherein a conversion of n-butene is at least 35 wt-%.

* * * * *